(12) United States Patent
Zhao et al.

(10) Patent No.: US 7,049,301 B2
(45) Date of Patent: May 23, 2006

(54) QUERCETIN DERIVATIVES AND THEIR MEDICAL USAGES

(75) Inventors: Yimin Zhao, Beijing (CN); Ming Yang, Beijing (CN); Yunfeng Li, Beijing (CN); Xinhui Luan, Beijing (CN); Zhipu Luo, Beijing (CN)

(73) Assignee: Academy of Military Medical Sciences Institute of Pharmacology and Toxicology, Beijing (CN)

( * ) Notice: Subject to any disclaimer, the term of this patent is extended or adjusted under 35 U.S.C. 154(b) by 0 days.

(21) Appl. No.: 10/673,030

(22) Filed: Sep. 26, 2003

(65) Prior Publication Data

US 2004/0132671 A1 Jul. 8, 2004

Related U.S. Application Data

(63) Continuation of application No. PCT/CN02/00198, filed on Mar. 3, 2002.

(60) Provisional application No. 60/278,841, filed on Mar. 26, 2001.

(51) Int. Cl.
*A01N 43/04* (2006.01)

(52) U.S. Cl. .................. 514/27; 514/33; 536/4.1; 536/18.1

(58) Field of Classification Search ............... 514/27, 514/33; 536/4.1, 18.1
See application file for complete search history.

(56) References Cited

FOREIGN PATENT DOCUMENTS

| CN | 1232675 | 10/1999 |
|----|---------|---------|
| CN | 1288896 | 3/2001  |

OTHER PUBLICATIONS

Yun-Feng, Li et al. "Antidepressant effect of quercetin 3-O-apiosyl (1→2)—[rhamnosyl (→6)]-glucoside in mice." Chinese Journal of Pharmacology and Toxicology, 14(2) (2000) pp. 125-127.

*Primary Examiner*—Elli Peselev
(74) *Attorney, Agent, or Firm*—Ladas and Parry LLP

(57) ABSTRACT

This invention relates to quercetin derivative, its preparation, and a pharmaceutical combination, as well as their medical uses for the prevention or treatment of diseases related to $5HT_{1A}$ receptor or neuron cell damages, including Alzeheimer's disease, drug or alcohol dependence, sleep disorders or panic state; and for delaying senility, improving learning and memory, preventing and treatment of neuron cell damages caused by various kinds of cerebral damages.

15 Claims, No Drawings

QUERCETIN DERIVATIVES AND THEIR MEDICAL USAGES

This application is a continuation of PCT/CN02/00198 filed Mar. 3, 2002.

The present application claims priority form U.S. patent application Ser. No. 60/278,841 filed on Mar. 26, 2001, which is incorporated herein by reference.

FIELD OF THE INVENTION

This invention relates to a quercetin derivative, its preparation and the medicinal composition containing the same, as well as medical uses thereof for the prevention or treatment of diseases related to $5HT_{1A}$ receptor

BACKGROUND OF THE INVENTION

The most common diseases related to $5HT_{1A}$ receptor are anxiety, depression and Alzeheimer's disease, etc. Medicines commonly used to treat diseases related to $5HT_{1A}$ receptor are conjugation agents of $5HT_{1A}$ receptor, such as artificially synthesized buspirone, desipramine, etc. However, these synthesized pharmaceuticals have common disadvantages, as they can do damages to liver, kidney and other human organs. Further more, patients suffering said diseases have to take dose for a long time, which makes much more obvious the side effects of said pharmaceuticals.

Apparently, searching for new, natural, high effective while glandless conjugation agents of $5HT_{1A}$ receptor has been the focus in the field of new pharmaceuticals.

DESCRIPTION OF THE INVENTION

Through extensive and intensive researches, inventors of this invention find that quercetin derivatives, as shown in formula I, can serve as the ligand of $5HT_{1A}$ receptor, which can protect neuron cells and exhibit favorable activities of treating and preventing diseases and symptoms related to $5HT_{1A}$ receptor, such as depression, anxiety, Alzeheimer's disease, drug or alcohol dependence, sleep disorders; of protecting neuron cells, delaying senility, improving learning and memory, preventing and treating panic state due to neuron cell damages induced by various kinds of cerebral damages, anti-gastric and duodenal ulcer, and of adjustment for heart and blood pressure, etc.

Formula I:

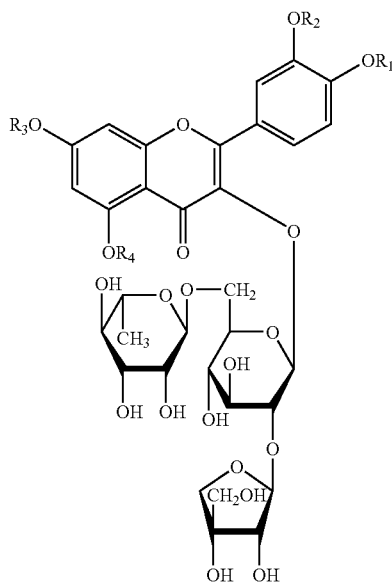

wherein $R_1$, $R_2$, $R_3$, $R_4$ are all or partly hydrogen atoms or alkyl containing 1 to 5 carbon atoms.

The compound in formula I, when $R_1$, $R_2$, $R_3$, $R_4$ are all hydrogen atoms, is quercetin-3-O-β-D-apiofuranosyl-(1→2)-[α-D-rhamnopyranosyl-(1→6)]-β-D-glucopyranoside.

Quercetin-3-O-β-D-apiofuranosyl-(1→2)-[α-D-rhamnopyranosyl-(1→6)]-β-D-glucopyranoside is a compound extracted from glandless cottonseeds by inventors of the invention through extensive study. Glandless cotton is a crop breed selected and cultivated from upland cotton of Malvaceae (Gossypium Hirsutum L.). Glandless cottonseeds are the mature seeds of glandless cotton, which are generally used as livestock feedstuff. Said compound can also be extracted from normal cottonseeds.

The inventors of the invention have for the first time separated and extracted from glandless cottonseeds the biologically active chemical monomer, identified the chemical structure of said extract and developed the medical uses of said chemical monomer and its derivatives. The present invention is achieved based on the above-mentioned discoveries.

So far, there is no other research reported on the extraction of quercetin derivatives from glandless cottonseeds or synthesis of quercetin derivatives as shown in Formula I, nor has any research on bioactivities of quercetin derivatives as shown in formula I been reported.

The inventors of the invention prepare alkyl derivatives of quercetin as shown in formula I by alkylation reaction, and find that the alkyl derivative of quercetin-3-O-β-D-apiofuranosyl-(1→2)-[α-D-rhamnopyranosyl-(1→6)]-β-D-glucopyranoside as shown in formula I, can equally serve as the ligand of $5HT_{1A}$ receptor and have protective effect on neuron cells, and exhibit favorable activities of treating and preventing diseases and symptoms related to $5HT_{1A}$ receptor, such as depression, anxiety, Alzeheimer's disease, drug or alcohol dependence, sleep disorders; of protecting neuron cells, delaying senility, improving learning and memory, preventing and treating panic state due to neuron cell damages induced by various kinds of cerebral damages, anti-gastric and duodenal ulcer, and of adjustment for heart and blood pressure, etc.

Quercetin derivatives according to the invention as shown in formula I have no toxic side effects frequently occurring for synthesized pharmaceuticals. Therefore, the present invention possesses prominent substantive features and notable progress as compared with prior art.

The present invention relates to compound of formula I, useful as protective agent of neuron cells and with favorable activities of preventing or treating diseases related to $5HT_{1A}$ receptor and neuron cells damages; of protecting neuron cells, delaying senility, improving learning and memory, as well as of preventing and treating neuron cell damages induced by various kinds of cerebral damages, etc.

The present invention further relates to a pharmaceutical composition comprising compound of formula I and pharmaceutical carriers.

The present invention further relates to compound of formula I for preventing or treating diseases or symptoms related to $5HT_{1A}$ receptor, especially for preventing and treating depression, anxiety, Alzeheimer's disease, drug or alcohol dependence, sleep disorders, as well as for protecting neuron cells, delaying senility, improving learning and memory, preventing and treating diseases related to neuron cell damages induced by various kinds of cerebral damages.

The present invention further relates to a pharmaceutical composition comprising compound of formula I, for preventing or treating diseases or symptoms related to $5HT_{1A}$ receptor, especially for preventing and treating depression, anxiety, Alzeheimer's disease, drug or alcohol dependence, sleep disorders, as well as for protecting neuron cells, delaying senility, improving learning and memory, preventing and treating diseases related to neuron cell damages induced by various kinds of cerebral damages.

According to the present invention, compound of formula I and pharmaceutical composition thereof, of the present invention, can be administered orally, parenterally or topically. The dosage form may be, for example, tablets, capsules, solutions, suspensions, injections and intravenous dripping solutions, etc.

According to the present invention, quercetin-3-O-β-D-apiofuranosyl-(1→2)-[α-D-rhamnopyranosyl-(1→6)]-β-D-glucopyranoside of formula I is obtained, for example, from glandless cottonseeds.

The extraction of quercetin-3-O-β-D-apiofuranosyl-(1→2)-[α-D-rhamnopyranosyl-(1→6)]-β-D-glucopyranoside from glandless cottonseeds can be carried out by means of, for example organic solvent extraction and separation. The organic solvents employed include alcohols, such as methanol, ethanol, propanol, butanol; halogenated hydrocarbons such as methylene dichloride, chloroform; esters such as methyl acetate, ethyl acetate, propyl acetate; and ethers such as petroleum ether, ethyl ether. The separation materials employed during the separation can be silica gel, polyamide, etc.

According to the present invention, alkyl derivatives of quercetin-3-O-β-D-apiofuranosyl-(1→2)-[α-D-rhamnopyranosyl-(1→6)]-β-D-glucopyranoside of formula I can be prepared by the reaction in alkaline alcoholic solution between quercetin-3-O-β-D-apiofuranosyl-(1→2)-[α-D-rhamnopyranosyl-(1→6)]-β-D-glucopyranoside and calculated amount of alkyl halide.

The pharmaceutical composition of the invention can be prepared according to known methods in the art, for example by mixing compound of formula I with pharmaceutical carriers.

The following examples and bioactivity experiments further illustrate the present invention and are not intended to limit the invention in any way.

EXAMPLE 1

Preparation of Quercetin-3-O-β-D-apiofuranosyl-(1→2)-[α-D-rhamnopyranosyl-(1→6)]-β-D-glucopyranoside 1 kg of glandless cottonseeds are crushed and then passed through a 100 mesh, followed by 3 times of extraction with 5 L petroleum ether for each time. The residues are then extracted 3 times with ethanol, 8 L for each time. The extraction solution is then merged and evaporated under reduced pressure to constant weight. The 260 g of ethanol extract obtained is then dissolved in water, and distributed in n-butanol/$H_2O$ solution, to give 10 g of n-butanol extract and 200 g of water extract. The n-butanol extract is separated through a silica gel column to give the compound of formula I, the developing agent is n-butanol:acetic acid:$H_2O$=7:1:2.

The compound of formula I thus obtained is yellow powder and turns into dark-red when heated in 10% EtOH-$H_2SO_4$, which indicates the existence of saccharide. Bright white fluorescence observed at 254 nm, indicates itself being a flavonoid. Absorption peaks in IR spectrum (KBr) of said compound, of 3412 cm$^{-1}$ ($v_{-OH}$), 2925 cm$^{-1}$, 1654 cm$^{-1}$ ($v_{-C=O}$), 1608 cm$^{-1}$, 1361 cm$^{-1}$, 1202 cm$^{-1}$, indicate existence of hydroxy and carbonyl; the UV spectrum of said compound: 256.2 nm (log e 3.95), 354.6 nm (log e 2.83), shows typical spectrum of a flavonol. The UV spectrum of said compound after adding shift reagent is shown in table 1, indicating that the aglucone of said compound is 3-O-substituted quercetin.

TABLE 1

UV spectrum data of compound of formula I

| | Band I | Band II | Results |
|---|---|---|---|
| MeOH | 354.5 | 257.0 | 3-O-substituted quercetin |
| MeONa | 403.5 | 270.5 | 4'-OH |
| AlCl$_3$ | 430.5 | 274.0 | 3',4'-OH |
| AlCl$_3$/HCl | 363.0 | 268.5 | 5-OH |
| NaAc | 396.5 | 268.5 | 7-OH |
| NaAc/H$_3$BO$_3$ | 374.0 | 260.0 | ring B with two adjacent hydroxyls |

The molecule weight of compound of formula I is determined to be 742 by FAB-MS, which indicates a m/z $[M+H]^+$ of 743. The ESI-MS/MS (m/z) of positive ions gives 743 $[M+H]^+$, 611, 597, 465, 303 (arctigenin), which indicates the existence of pentose, methyl-hexose and hexose, and that pentose and methyl-hexose locate at the end of the saccharide chain respectively.

NMR data of compound of formula I is shown in table 2.

TABLE 2

NMR data of compound of formula I (DMSO-d$_6$, 400 MHz)

| No. | | $^{13}$C | $^1$H | |
|---|---|---|---|---|
| Quercetin | 2 | 156.52 | | |
| | 3 | 132.81 | | |
| | 4 | 177.04 | | |
| | 5 | 161.23 | | |
| | 6 | 98.81 | 6.12 (1H, s) | 161.23 (5), 93.86 (8), 103.28 (10) |
| | 7 | 166.30 | | |
| | 8 | 93.86 | 6.30 (1H, s) | 98.81 (6) 103.28 (10), 156.10 (2) |
| | 9 | 156.10 | | |
| | 10 | 103.28 | | |
| | 1' | 121.87 | | |
| | 2' | 115.80 | 7.57 (1H, dd, 2.0 Hz, 1.6 Hz) | 120.80 (6'), 145.01 (3'), 147.00 (4'), |
| | 3' | 145.01 | | |
| | 4' | 147.00 | | |
| | 5' | 115.80 | 6.82 (1H, dd, 8.8 Hz, 1.6 Hz) | 120.80 (6'), 145.01 (3') |
| | 6' | 120.80 | 7.72 (1H, dd, 8.8 Hz, 2.0 Hz) | 115.80 (2'), 147.00 (4') |
| Glucose | 1 | 99.16 | 5.53 (1H, d, 7.6 Hz) | |
| | 2 | 76.99 | 3.52 (1H, d, 7.6 Hz) | 99.16 (1g), 108.64 (1a) |
| | 3 | 76.88 | | |
| | 4 | 70.36 | | |
| | 5 | 75.69 | | |
| | 6 | 66.88 | | |
| Rhamnose | 1 | 100.70 | 4.39 (1H, s) | 66.88 (6g), 70.55 (3r), 68.30 (5r) |
| | 2 | 70.30 | 3.11 (1H, s) | 71.84 (4r), |
| | 3 | 70.55 | | |
| | 4 | 71.84 | 3.09 (1H, s) | |
| | 5 | 68.30 | | |
| | 6 | 17.78 | 1.01 (3H, d, 6.2 Hz) | |
| Apiose | 1 | 108.64 | 5.39 (1H, d, 1.3 Hz) | 79.33 (3a), 74.01 (4a) |
| | 2 | 76.17 | 3.85 (br d) | |
| | 3 | 79.33 | — | |
| | 4 | 74.01 | 3.87 (br d,) | |
| | 5 | 64.34 | 3.40 (br d) | |

EXAMPLE 2

Preparation of 5,7,3',4'-tetraethoxyl Flavonol-3-O-β-D-apiofuranosyl-(1→2)-[α-D-rhamnopyranosyl-(1→6)]-β-D-glucopyranoside 1.2 g (1.6 mmol) of compound of formula I and 6.5 mmol of bromoethane are dissolved in 30 ml of anhydrous alcohol, and the solution obtained is then transferred to a 100 ml three-necked flask equipped with a reflux condenser pipe, a stirrer, an inside thermometer and a drip funnel. After addition of alcohol solution containing 6.5 mmol of sodium ethylate while stirring, the mixture is allowed to react for 20~50 minutes under room temperature. The reactants are cooled, 20 ml of chloroform is then added dropwise. Allowed to stand, then NaBr is filtered off and the filtrate is concentrated to dryness under reduced pressure. The products are subjected to silica gel column separation, and eluted with chloroform/methanol (5:1) to give compound of formula I wherein $R_1$, $R_2$, $R_3$, $R_4$ are all ethyl, i.e. 5,7,3',4',-tetraethoxyl flavonol-3-O-β-D-apiofuranosyl-(1→2)-[α-D-rhamnopyranosyl-(1→6)]-β-D-glucopyranoside, with its molecule weight determined as 854 by FAB-MS m/z of 855$[M+H]^+$.

EXAMPLE 3

Experiments on Bioactivity of Compound According to the Invention: Quercetin-3-O-β-D-apiofuranosyl-(1→2)-[α-D-rhamnopyranosyl-(1→6)]-β-D-glucopyranoside 3.1 Effect on Activities of Adenylate Cyclase (AC) in Rat Cerebral Cortex:

(1) Methods and Results

Male Wistar rats weighed 200±20 g are sacrificed by decollation, and cerebral cortex is separated. Synaptolemma is extracted at 4° C. according to the method as described in literature (Rasenick M M et al, Pro. Natl. Acad. Sci. USA, 1980; 77:4628) and suspended in buffer solution, so that a protein concentration of 3~5 mg/ml is reached. The synaptolemma has to be incubated in advance with the test medicine, as adenylate cyclase (AC) is located on it. The experiment is carried out as follows: portions of 100 μl reaction solution containing certain concentration of test medicine and 15 mmol/L HEPES, pH=7.5, 5 mmol/L $MgCl_2$, 1 mmol/L EGTA, 1 mol/L DTT, 60 mmol/L NaCl, 1 mmol/L aminophylline, 0.5 mg/ml phosphocreatine and 0.14 mg/ml phosphocreatine kinase are respectively dispensed into reaction tubes, followed by addition of 20 μg synaptolemma to each tube. Then, the tubes are immediately put into a water-bath at 30° C. to react for 10 minutes, which reaction is linear during the first 20 minutes. After that, all the reaction tubes are immediately transferred into boiling water and deposited for 3 minutes to terminate the reaction. The amount of cAMP thus produced is measured in an ice-bath environment with cAMP kit, the total reaction volume is 130 μL. The measure is carried out according to the instruction of the kit: various reagents are added and, after the reaction finishes, the tubes are centrifugated at 4000 rpm for 7 minutes. 120 μl supernatant is then pipetted into the measure cup, added afterwards with 1.5 ml anhydrous alcohol, after shaken up, 3.5 ml of scintillation solution is added. Then, the cups are sealed and shaken up, and are left overnight. The values of CMP of all samples are determined then by Wallac 1409 liquid scintillation counter. The amount of cAMP produced can be calculated according to the standard curve and CPM. The results are statistically analyzed by ANOVA, and Dunnett's T test is made for inter-group comparison. The results are shown in table 3 and table 4.

TABLE 3

Activation effect of imipramine and buspirone on AC

| | Amount of cAMP produced (pmol/mg protein/minute) | | | |
|---|---|---|---|---|
| Medicines | 25 μM | 100 μM | 400 μM | 1 mM |
| imipramine | 15.07 ± 4.91 | 18.53 ± 3.2* | 30.32 ± 5.63*** | 79.79 ± 21.38*** |
| buspirone | 19.52 ± 5.46* | 19.71 ± 5.57* | 24.63 ± 3.49*** | 33.00 ± 8.58*** |
| physiological saline | 13.47 ± 1.92 | — | — | — |

X ± SD vs control group,
*$P < 0.05$,
***$P < 0.001$

TABLE 4

Activation effect of compound of formula I on AC

| | Amount of cAMP produced (pmol/mg protein/minute) | | | |
|---|---|---|---|---|
| Medicines | 13.5 μM | 40.5 μM | 135 μM | 405 μM |
| Compound of formula I | 23.27 ± 4.95* | 4.75 ± 6.33*** | 43.42 ± 4.78*** | 68.34 ± 10.45*** |
| physiological saline | 13.47 ± 1.92 | — | — | — |

X ± SD vs control group,
*$P < 0.05$,
***$P < 0.001$ (2) Discussion

It is indicated that anti-depression agent has an acute activation effect on synaptolemma AC, which might be an important step of its mechanism. It can be drawn from table 1 that typical anti-depression agent imipramine and non-typical anti-depression agent buspirone dose-dependently activate AC. The compound of formula I remarkably activate AC under a concentration of only 13.5 μM (0.01 mg/ml), up to 23.27±4.95 pmol/mg protein/minute, which effect is stronger than those of 25 μM imipramine and buspirone. The activation effect of said compound at 404 μM (0.3 mg/ml) amounts up to 68.34±10.45 pmol/mg protein/minute, 2~3 times higher than same doses of imipramine and buspirone. Therefore, it can be concluded that compound of formula I has an anti-depression effect with relatively higher activity.

3.2. Protection Effect of Compound of Formula I on PC-12 Cells Damaged by Corticosterone.

(1) Methods and Results

PC-12 cells are diluted into a suspension (2×10⁵ cells/ml) with DMEM culture solution containing 5% calf serum and 5% horse serum, and then are transplanted into 96-well plates pretreated with polylysine, and cultivated under conditions of 37° C. and 5% $CO_2$ for 2~3 days. Cells are to grow all over the wells bottom before test. The culture solution is then pipetted away and serum-free DMEM is added containing certain concentration of test medicine and $10^{-4}$ mol/L corticosterone, 10 μl of 5 mg/ml MTT is added 48 hours later to each well, shaking up slightly and, 4 hours later, 100 μl of 10% SDS is added to each well, again shaking up slightly. The plates are then left in the incubator overnight at 37° C.(about 8~12 hours). After all the dark-blue crystals are dissolved, shaking up slightly and absorbance (A) of each sample at 570 nm is read using microplate reader. The results are then statistically analyzed by ANOVA, and shown in table 5.

TABLE 5

Protection effect of compound of formula I on PC-12 cells damaged by corticosterone

| Medicines (μ mol · $L^{-1}$) | Absorbance (A) | Increase of A (%) |
|---|---|---|
| Normal control | 0.77 ± 0.12 | |
| Damaged control | 0.24 ± 0.04 | |
| Compound of formula I | | |
| 4.04 | 0.74 ± 0.14** | 208.3 |
| 14.38 | 0.84 ± 0.08*** | 250.0 |
| 40.43 | 0.86 ± 0.10*** | 258.3 |
| 134.77 | 0.77 ± 0.11*** | 220.8 |
| 404.31 | 0.61 ± 0.16** | 154.2 |

X ± SD vs damaged control,
**$P < 0.01$,
***$P < 0.001$ (2) Discussion

Data in table 5 shows that the increase of A (%) of compound of formula I reaches as high as 208.3%, at a concentration of 4.04 μmol/L. The higher the increase of A, the stronger the protection effect of said compound to PC-12 cells damaged by corticosterone. Therefore, said compound has a strong protection effect on PC-12 cells (rat pheochromocytoma cell strain) damaged by corticosterone, which is identical with the effect thereof on primary cultured hippocampal cells.

The experiment shows that the compound of formula I has a conspicuous protection effect on neuron cells.

3.3 Forced Swimming Test (1) The test is carried out according to literature (Arch Int. Pharmacodn. Ther, 1977, 229(2): 327). 30 minutes after abdominal injection or 60 minutes after oral administration, the mice are put into an open glass box (19 cm high and 12 cm of diameter). Water inside the glass box is 8 cm in depth and 22~23° C. in temperature. The mice are put into the water for 6 minutes and observed by Vidio movement analyzer, the accumulated immobility time of the mice during the last 4 minutes and their activity are analyzed identically as above. The results are shown in table 6 and table 7.

TABLE 6

Effect of abdominal administration of compound of formula I on forced swimming behavior of mice

| Medicines | Duration of immobility (sec) |
|---|---|
| physiological saline | 184.94 ± 19.15 |
| Compound of formula I (mg/kg) | |
| 0.31 | 148.69 ± 30.81* |
| 1.25 | 149.94 ± 34.87* |
| 5.00 | 134.38 ± 40.99** |

X ± SD vs control group,
*$P < 0.05$,
**$P < 0.001$

TABLE 7

Effect of compound of formula I administered orally on forced swimming behavior of mice

| Medicines | Dosage(mg/kg) | Number of animal | immobility time (sec) |
|---|---|---|---|
| Control | — | 20 | 93.6 ± 48.2 |
| Compound | 3.75 | 15 | 95.2 ± 47.4 |
| of formula I | 7.5 | 14 | 62.2 ± 45.9* |
| | 15 | 13 | 53.6 ± 50.8* |
| | 30 | 12 | 111.5 ± 52.9 |

X ± SD vs control group,
*$P < 0.05$ (2) Discussion

Table 6 and table 7 show that compound of formula I can shorten the immobility time of mice at a dosage of 0.31 mg/kg administered abdominally or at a dosage of 7.5 mg/kg administered orally. Therefore, said compound has relatively high anti-depression activity.

5,7,3',4',-tetraethoxyl flavonol-3-O-β-D-apiofuranosyl-(1→2)-[α-D-rhamnopyranosyl-(1→6)]-β-D-glucopyranoside (compound of formula I wherein $R_1$, $R_2$, $R_3$, $R_4$ are all ethyl), when administered orally, exhibits a similar anti-depression effect as compound of formula I in the forced swimming behavior test of mouse.

3.4 $5HT_{1A}$ Receptor Test (1) Method

20 μl of $^3$H-8-OH-DPAT (20 mmol) and 20 μl of sample solutions of different concentrations are added into 50 μl of 1:5 suspension of rat hippocampal membrane receptor, followed by addition of buffer solution to make up to final volume of 200 μL. Then the above-mentioned suspension is shaken up and incubated in a water-bath at 25° C. for 30 minutes. After quick filtration by suction and washing the membrane receptors, radioactivity value is read by liquid scintillation counter. 20 μl of 5HT inosine sulfate (1 mmol) solution is used instead to determine the non-specific conjugation. Buspirone, a partially activating agent of $5HT_{1A}$ receptor, is used as the positive control. The competitive inhibition rate of the sample to $^3$H-8-OH-DPAT is calculated according to the radioactivity value.

(2) Results $IC_{50}$ of compound of formula I is about 50 $pmol.L^{-1}$.

$IC_{50}$ of 5,7,3',4',-tetraethoxyl flavonol-3-O-β-D-apiofuranosyl-(1→2)-[α-D-rhamnopyranosyl-(1→6)]-β-D-glucopyranoside (compound of formula II wherein $R_1$, $R_2$, $R_3$, $R_4$ are all ethyl) is about 200 $pmol.L^{-1}$.

The invention claimed is:

1. A purified compound of formula I

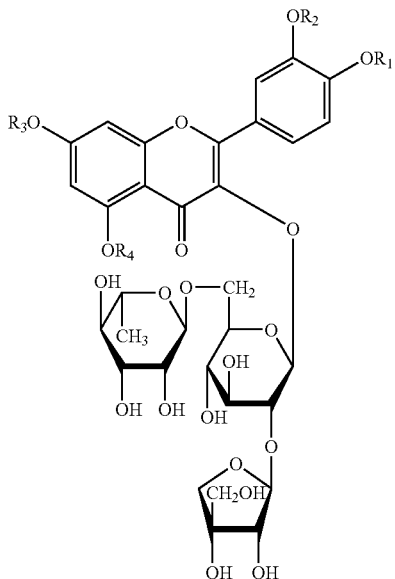

wherein $R_1$, $R_2$, $R_3$, $R_4$ are all or partly hydrogen atoms, or alkyl containing 1 to 5 carbon atoms; or pharmaceutically acceptable salts thereof.

2. Compound of formula I according to claim 1, wherein $R_1$, $R_2$, $R_3$, $R_4$ are all hydrogen atoms.

3. Compound of formula I according to claim 2, characterized in that the compound is derived from cottonseeds.

4. Compound of formula I according to claim 1, which is quercetin-3-O-β-D-apiofuranosyl-(1→2-[α-D-rhamnopyranosyl-(1→6)]-β-D- glucopyranoside.

5. A pharmaceutical composition comprising compound of formula I,

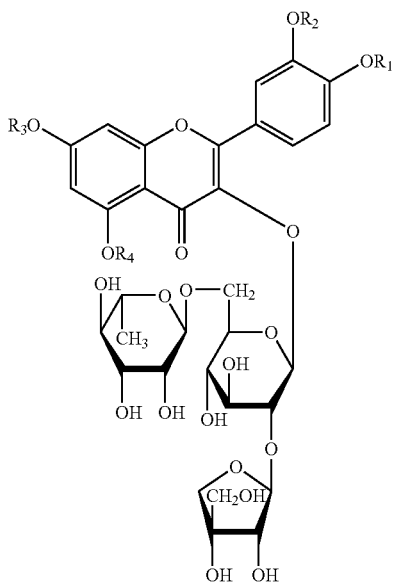

wherein $R_1$, $R_2$, $R_3$, $R_4$ are all or partly hydrogen atoms, or alkyl containing 1 to 5 carbon atoms; and a pharmaceutical carrier.

6. Pharmaceutical composition according to claim 5, for the treatment of diseases or symptoms related to $5HT_{1A}$ receptor,.

7. Pharmaceutical composition according to claim 5, for protection of neuron cells.

8. Pharmaceutical composition according to claim 5, wherein the pharmaceutical carriers are adjuvants for use in solid medicaments including disintegrants, diluting agents, binders, lubricants, and those for use in liquid medicaments including solvents, pH adjusting agents, osmotic regulators, antioxidants, metal complexing agents, preservatives, flavoring agents, and mixtures thereof.

9. Pharmaceutical composition according to claim 5, wherein $R_1$, $R_2$, $R_3$, $R_4$ of formula I are all hydrogen atoms.

10. Method of treating a disease related to $5HT_{1A}$ acceptor or for protection of neuron cells which comprises administering to a patient in need thereof a therapeutically effective amount of a compound of formula I,

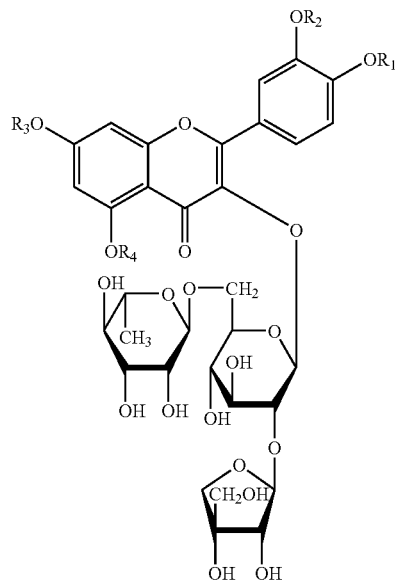

wherein $R_1$ $R_2$, $R_3$ and $R_4$ are all or partly hydrogen atoms or alkyl containing 1 to 5 carbon atoms.

11. Method according to claim 10, wherein $R_1$, $R_2$, $R_3$, $R_4$ of formula I are all hydrogen atoms.

12. Pharmaceutical composition according to claim 5 wherein the pharmaceutical carrier comprises an adjuvant for use in solid medicaments.

13. Pharmaceutical composition according to claim 12 wherein said adjuvant is selected from disintegrants, diluting agents, binders, lubricants or mixtures thereof.

14. Pharmaceutical composition according to claim 5 wherein the pharmaceutical carrier comprises an adjuvant for use in liquid medicaments.

15. Pharmaceutical composition according to claim 14 wherein said adjuvant is selected from solvents, pH adjusting agents, osmotic regulators, antioxidants, metal complexing agents, preservatives, flavoring agents or mixtures thereof.

* * * * *